United States Patent
Bosnyak et al.

(10) Patent No.: US 12,291,058 B2
(45) Date of Patent: May 6, 2025

(54) DISPERSIONS FOR ADDITIVE MANUFACTURING COMPRISING DISCRETE CARBON NANOTUBES

(71) Applicant: MOLECULAR REBAR DESIGN, LLC, Austin, TX (US)

(72) Inventors: Clive P. Bosnyak, Dripping Springs, TX (US); Kurt W. Swogger, Austin, TX (US); Steven Lowder, Gilbert, AZ (US); Olga Ivanova, Queen Creek, AZ (US)

(73) Assignee: MOLECULAR REBAR DESIGN, LLC., Austin, TX (US)

( * ) Notice: Subject to any disclaimer, the term of this patent is extended or adjusted under 35 U.S.C. 154(b) by 978 days.

(21) Appl. No.: 17/212,612

(22) Filed: Mar. 25, 2021

(65) Prior Publication Data

US 2021/0237509 A1 Aug. 5, 2021

Related U.S. Application Data

(63) Continuation-in-part of application No. 17/187,658, filed on Feb. 26, 2021, which is a continuation-in-part of application No. 16/012,265, filed on Jun. 19, 2018, now Pat. No. 10,934,447, which is a continuation-in-part of application No. 15/288,553, filed on Oct. 7, 2016, now Pat. No. 9,636,649, which is a continuation-in-part of application No. 15/225,215, filed on Aug. 1, 2016, now Pat. No. 9,493,626, which is a continuation-in-part of application No. 15/166,931, filed on May 27, 2016, now Pat. No. 9,422,413, which is a continuation of application No. 14/924,246, filed on Oct. 27, 2015, now Pat. No. 9,353,240, which is a continuation of application No. 13/993,206, filed as application No. PCT/EP2011/072427 on Dec. 12, 2011, now Pat. No. 9,212,273.

(60) Provisional application No. 61/423,033, filed on Dec. 14, 2010.

(51) Int. Cl.
| | | |
|---|---|---|
| B60C 1/00 | (2006.01) |
| A61K 47/69 | (2017.01) |
| A61K 49/00 | (2006.01) |
| A61K 51/12 | (2006.01) |
| B82Y 30/00 | (2011.01) |
| B82Y 40/00 | (2011.01) |
| C01B 32/174 | (2017.01) |
| C08C 1/14 | (2006.01) |
| C08J 3/205 | (2006.01) |
| C08K 3/04 | (2006.01) |
| C08K 7/06 | (2006.01) |
| C09K 23/00 | (2022.01) |
| C08L 7/00 | (2006.01) |
| C08L 9/06 | (2006.01) |
| C08L 9/08 | (2006.01) |

(52) U.S. Cl.
CPC ............ *B60C 1/00* (2013.01); *A61K 47/6905* (2017.08); *A61K 47/6949* (2017.08); *A61K 49/0076* (2013.01); *A61K 51/1217* (2013.01); *A61K 51/1275* (2013.01); *B82Y 30/00* (2013.01); *B82Y 40/00* (2013.01); *C01B 32/174* (2017.08); *C08C 1/14* (2013.01); *C08J 3/2053* (2013.01); *C08K 3/041* (2017.05); *C08K 7/06* (2013.01); *C09K 23/002* (2022.01); *C01P 2004/54* (2013.01); *C08J 2321/02* (2013.01); *C08K 2201/011* (2013.01); *C08K 2201/016* (2013.01); *C08L 7/00* (2013.01); *C08L 9/06* (2013.01); *C08L 9/08* (2013.01)

(58) Field of Classification Search
CPC .. B60C 1/00; C08K 3/041; C08K 7/06; C08K 2201/011; C08K 2201/016; C01B 32/174; A61K 47/6905; A61K 47/6949; A61K 49/0076; A61K 51/1217; A61K 51/1275; C09K 23/002; B82Y 30/00; B82Y 40/00; C08C 1/14; C08J 3/2053; C08J 2321/02; C01P 2004/54; C08L 7/00; C08L 9/06; C08L 9/08
USPC ......................................................... 524/241
See application file for complete search history.

(56) References Cited

U.S. PATENT DOCUMENTS

| | | |
|---|---|---|
| 3,471,395 A | 10/1969 | Summer |
| 4,421,878 A | 12/1983 | Close |
| 4,625,761 A | 12/1986 | Uchida |
| 5,079,123 A | 1/1992 | Nanya |

(Continued)

FOREIGN PATENT DOCUMENTS

| | | |
|---|---|---|
| CN | 1402888 A | 3/2003 |
| EP | 2139630 B1 | 5/2013 |

(Continued)

OTHER PUBLICATIONS

International Search Report and Written Opinion dated Aug. 2, 2022 issued in PCT/US2022/21737 filed on Mar. 24, 2022.

(Continued)

*Primary Examiner* — Ling Siu Choi
*Assistant Examiner* — Ronald Grinsted
(74) *Attorney, Agent, or Firm* — HUNTON ANDREWS KURTH LLP

(57) ABSTRACT

The present invention is directed to additive manufacturing compositions and methods for producing additive manufacturing composite blends with oxidized discrete carbon nanotubes with dispersion agents bonded to at least one sidewall of the oxidized discrete carbon nanotubes. Such compositions are especially useful when radiation cured, sintered or melt fused.

17 Claims, No Drawings

(56) References Cited

U.S. PATENT DOCUMENTS

| | | | |
|---|---|---|---|
| 5,458,681 | A | 10/1995 | Hasegawa |
| 5,750,304 | A | 5/1998 | Yamaguchi |
| 6,544,326 | B1 | 4/2003 | Itou |
| 6,569,231 | B1 | 5/2003 | Mathias |
| 6,783,746 | B1 | 8/2004 | Zhang et al. |
| 7,091,120 | B2 | 8/2006 | Buretea |
| 7,163,973 | B2 | 1/2007 | Ahsan |
| 7,601,421 | B2 | 10/2009 | Khabashesku et al. |
| 7,749,682 | B2 | 7/2010 | Miyabe |
| 7,763,229 | B2 | 7/2010 | Nikolaev et al. |
| 7,807,127 | B1 | 10/2010 | Forohar |
| 7,846,998 | B2 | 12/2010 | Akagi |
| 7,959,280 | B2 | 6/2011 | Koike |
| 8,282,725 | B2 | 10/2012 | Shimomura |
| 9,327,054 | B2 | 5/2016 | Sundara |
| 9,636,649 | B2 | 5/2017 | Bosnyak et al. |
| 10,000,653 | B2 | 6/2018 | Swogger et al. |
| 2003/0049443 | A1 | 3/2003 | Nishimura et al. |
| 2003/0213939 | A1 | 11/2003 | Narayan |
| 2006/0014873 | A1 | 1/2006 | Ikezawa |
| 2006/0124028 | A1 | 6/2006 | Huang |
| 2007/0259994 | A1 | 11/2007 | Tour |
| 2008/0315453 | A1 | 12/2008 | Molitor |
| 2009/0168301 | A1 | 7/2009 | Viswanathan |
| 2009/0200517 | A1 | 8/2009 | El Bounia |
| 2010/0004468 | A1 | 1/2010 | Wong et al. |
| 2010/0006152 | A1 | 1/2010 | Hatton |
| 2010/0009165 | A1 | 1/2010 | Patel |
| 2010/0016473 | A1 | 1/2010 | Kaji |
| 2010/0122642 | A1* | 5/2010 | Farrugia .............. C09D 11/101 977/902 |
| 2010/0124713 | A1 | 5/2010 | Farrugia |
| 2010/0197832 | A1 | 8/2010 | Sun |
| 2010/0267883 | A1 | 10/2010 | Bhatt |
| 2011/0183253 | A1 | 7/2011 | Aga |
| 2011/0272856 | A1 | 11/2011 | Rasmussen |
| 2012/0035309 | A1 | 2/2012 | Zhu et al. |
| 2012/0058255 | A1 | 3/2012 | Gan |
| 2012/0183770 | A1 | 7/2012 | Bosnyak et al. |
| 2017/0050158 | A1 | 2/2017 | Bosnyak et al. |
| 2018/0298221 | A1 | 10/2018 | Swogger et al. |
| 2019/0161350 | A1 | 5/2019 | Swogger et al. |
| 2020/0018535 | A1 | 1/2020 | Leal et al. |
| 2020/0198973 | A1 | 6/2020 | Swogger et al. |
| 2020/0369522 | A1 | 11/2020 | Finlayson et al. |
| 2021/0179880 | A1 | 6/2021 | Swogger et al. |
| 2021/0237509 | A1 | 8/2021 | Bosnyak et al. |

FOREIGN PATENT DOCUMENTS

| | | |
|---|---|---|
| JP | 2009-235650 A | 10/2009 |
| KR | 10-2008-0111488 | 12/2008 |
| WO | 200135473 A1 | 5/2001 |
| WO | 2008054845 A2 | 5/2008 |
| WO | 2008067137 A2 | 6/2008 |
| WO | 2011163129 A2 | 12/2011 |

OTHER PUBLICATIONS

Chaturvedi, Poornendu et al., "Carbon Nanotube-Purification and Sorting Protocols" Defence Science Journal, vol. 58, No. 5, Sep. 2008, pp. 591-599.

Kim, Dong Sik et al., Individualization of Single-walled Carbon Nanotubes: Is the Solvent Important? Small, 2005, 1, No. 11, pp. 1117-1124.

International Search Report and Written Opinion dated May 3, 2022 issued in International Application No. PCT/US2022/017992.

J. Mijovic, E. M. Pearce, and C.-C. Foun. "Fluoroelastomer Modified Thermoset Resins." Advances in Chemistry; American Chemical Society 1984, 293-307.

P. C. Hiemenz, T.P. Lodge. "Polymer Chemistry, Second Edition." CRC Press 2007. Chapters 2 and 10.

B.D. Cullity. "Elements of X-Ray Diffraction." Addison-Wesley Publishing Company, Inc. 1978. p. 86-87.

J.E. Plevyak and L.A. Sobieski. "Improved RIM Processing with Silicone Internal Mold Release Technology." Journal of Cellular Plastics 1984, 363-368.

N. Canter. "Mold-release agents and coatings." Tribology & Lubrication Technology 2008, 31-38.

A. Hirsch. "Functionalization of Single-Walled Carbon Nanotubes" Angew. Chem. Int. Ed. 2002, 41, No. 11, 1853-1859.

"The IUPAC Rules for Naming Organic Molecules" Stanislaw Skonieczny. Journal of Chemical Education. vol. 83 No. 11, pp. 1633-1637 (2006) ("Skonieczny").

"Characterization of Zirconium Phosphate/Polycation Thin Films Grown by Sequential Adsorption Reactions" Hyuk-Nyun Kim, Steven W. Keller, Thomas E. Mallouk, Johannes Schmitt, and Gero Decher. Chem. Mater., vol. 9, No. 6, 1997.

"Sonochemical Oxidation of Multiwalled Carbon Nanotubes." Yangchuan Xing, Liang Li, Charles C. Chusuei, and Robert V. Hull. Langmuir 2005, 21, 4185-4190.

"Surface modified multi-walled carbon nanotubes in CNT/epoxycomposites." Florian H. Gojny, Jacek Nastalczyk, Zbigniew Roslaniec, Karl Schulte. Chemical Physics Letters 370 (2003) 820-824.

Peddini S.K. et al., Nanocomposites from styrene-butadiene rubber (SBR) and multiwall carbon nanotubes (MWCNT) part 1: Morphology and rheology, Polymer 55 (2014) pp. 258-270.

Datsyuk V. et al., Chemical oxidation of multiwalled carbon nanotubes, Carbon 46 (2008) pp. 833-840.

\* cited by examiner

DISPERSIONS FOR ADDITIVE MANUFACTURING COMPRISING DISCRETE CARBON NANOTUBES

CROSS-REFERENCE TO RELATED APPLICATIONS

This application is a continuation-in-part application of U.S. Ser. No. 17/187,658, filed Feb. 26, 2021, which itself is a continuation in part of U.S. Ser. No. 16/012,265 filed Jun. 19, 2018, now U.S. Pat. No. 10,934,447, which is a continuation in part of U.S. Ser. No. 15/288,553 filed Oct. 7, 2016, now U.S. Pat. No. 9,636,649, which was a continuation-in-part application of U.S. Ser. No. 15/225,215 filed Aug. 1, 2016, allowed Sep. 12, 2016 and issued as U.S. Pat. No. 9,493,626 which was a continuation-in-part application of U.S. Ser. No. 15/166,931 filed May 27, 2016 and issued as U.S. Pat. No. 9,422,413 which was a continuation of U.S. Ser. No. 14/924,246, filed Oct. 27, 2015 and issued as U.S. Pat. No. 9,353,240, which is a continuation of U.S. Ser. No. 13/993,206, filed Jun. 11, 2013 and issued as U.S. Pat. No. 9,212,273, which claims priority to PCT/EP2011/072427, filed Dec. 12, 2011, which claims benefit of U.S. provisional application 61/423,033, filed Dec. 14, 2010. All of the afore-mentioned U.S. applications and/or granted patents are expressly incorporated herein by reference. This application is also related to U.S. Ser. Nos. 62/319,599; 14/585,730; 14/628,248; and Ser. No. 14/963,845.

FIELD OF INVENTION

The present invention is directed to additive manufacturing compositions and methods for producing additive manufacturing composite blends with oxidized discrete carbon nanotubes with dispersion agents bonded to at least one sidewall of the oxidized discrete carbon nanotubes. Such compositions are especially useful when radiation cured, sintered or melt fused.

BACKGROUND OF THE INVENTION

Additive Manufacturing (AM) is an appropriate name to describe the technologies that build 3D objects by adding layer-upon-layer of material, the material generally being crosslinkable monomers or oligomers, polymers, metals, ceramics, and biocompatible materials. Common to AM technologies is the use of a computer, 3D modeling software (Computer Aided Design or CAD), machine equipment and layering material. Once a CAD sketch is produced, the AM equipment reads in data from the CAD file and lays downs or adds successive layers of liquid, powder, sheet material or others such tape, in a layer-upon-layer fashion to fabricate a 3D object. The term AM encompasses many technologies including subsets like 3D Printing, Rapid Prototyping (RP), Direct Digital Manufacturing (DDM), layered manufacturing and additive fabrication.

Liquid radiation curable resins are selectively crosslinked (or cured) by an energy source such as lasers. Photocurable resin formulation efforts have focused on mechanical performance enhancement to simulate properties of commodity plastics and engineered polymers. Improving mechanical performance of photo-curable resins can be accomplished through development of special monomers and curing agents, altering chain growth mechanisms, utilization of mixed modes of polymerization and inclusion of additives and fillers. However, there remains many limitations as their balance of properties such as heat distortion resistance, rigidity, and impact strength.

Addition of fillers have been utilized to meet specific performance requirements for select AM applications, such as stiffness. Inorganic fillers such as $SiO_2$ and $Al_2O_3$ have shown to improve the strength and stiffness of the components fabricated via vat photopolymerization, but often with much longer undesirable cure times. In addition, these fillers often cause high initial resin viscosity, poor viscosity stability, and exhibit a tendency of filler to separate from the base resin. There is a continued need for fillers which do not cause undesirable additional cure times to the base crosslinkable resin formulation.

Hence there is a need for radiation curable resins that produce parts with enhanced mechanical, thermal, electrical, magnetic and chemical properties and satisfy stringent polymerization resin requirements such as high rates of curing, low viscosity, exceptional stability, and high green strength. In particular, it has been a challenge to reach a resistance of at least 10 billion ohm per square with conductive carbon blacks because of the above-mentioned rate of curing requirements.

For AM methods utilizing powdered material (metal, ceramic, or polymer) it is desired to improve their ability to sinter and also their green strength before secondary processing. Binder selection is considered essential for successful part fabrication. First, the binder must be jettable. An ideal binder has low viscosity, is stable under shear stresses, has good interaction with powdered feedstock, has a clean burn-out, has long shelf-life. Common in-liquid binding agents are butyral resins, polyvinyls, polysiloxanes, polyacrylic acids, and polyether-urethanes. It is desirable in some cases for a higher strength polymeric binder particularly where the sintering is occurring at higher temperatures.

Binders for metallic and ceramic powders are typically aqueous or non-aqueous dispersions of inorganic particles such as silica, aluminum nitrate or film forming polymer dispersions. The incorporation of nanoparticles into the binder system fills the voids in the packed powder bed and therefore improves sinterability, increases part density and reduces shrinkage. The melting point of nanoparticles decreases exponentially with a decrease in nanoparticle size. Therefore, nanoparticles in the binder will sinter at lower temperature than the feedstock powder and can fuse the large particles, thus improving green strength of the component. It is desirable to have a binder that has low ash residual content at the temperature of sintering or curing for metals, cermats or ceramics.

Binder for polymeric powders, typically consist of the solvent or a solvent mixture that promote swelling of the polymeric feedstock leading to particle coalescence by interdiffusion and entanglement. Solutions of film forming polymeric dispersions can be used as binders as well. Processing hydrophilic powders such as starch, plaster, and cement require aqueous binders. Hydrophobic polymer powders (e.g., polylactic acid or PLA) can be processed using organic solvents. These types of binders for polymeric powders can also be used to coat thermoplastic filaments for fusion into parts.

Carbon nanotubes can be classified by the number of walls in the tube, single-wall, double wall and multiwall. Each wall of a carbon nanotube can be further classified into chiral or non-chiral forms. Some of the carbon atoms of the carbon nanotube may be substituted by nitrogen atoms. Carbon nanotubes are currently manufactured as agglomerated carbon nanotube balls or bundles which have very limited commercial use. Use of carbon nanotubes as a reinforcing agent in polymer composites is an area in which carbon nanotubes are predicted to have significant utility. However, utilization of carbon nanotubes in these applications has been hampered due to the general inability to reliably produce individualized carbon nanotubes. To reach the full potential of performance enhancement of carbon nanotubes as composites in polymers the aspect ratio, that is length to diameter ratio, should be greater than 10. The maximum aspect ratio for a given tube length is taken to be reached when each tube is fully separated from another. A bundle of carbon nanotubes, for example, has an effective aspect ratio in composites of the average length of the bundle divided by the bundle diameter.

Various methods have been developed to debundle or disentangle carbon nanotubes in solution. For example, carbon nanotubes may be shortened extensively by aggressive oxidative means and then dispersed as individual nanotubes in dilute solution. These tubes have low aspect ratios not suitable for high strength composite materials. Carbon nanotubes may also be dispersed in very dilute solution as individuals by sonication in the presence of a surfactant. Illustrative surfactants used for dispersing carbon nanotubes in aqueous solution include, for example, sodium dodecyl sulfate, or cetyltrimethyl ammonium bromide. In some instances, solutions of individualized carbon nanotubes may be prepared from polymer-wrapped carbon nanotubes. Individualized single-wall carbon nanotube solutions have also been prepared in very dilute solutions using polysaccharides, polypeptides, water-soluble polymers, nucleic acids, DNA, polynucleotides, polyimides, and polyvinylpyrrolidone, but these dilute solutions are unsuitable for additive manufacturing.

SUMMARY OF INVENTION

The present invention relates to novel compositions and methods for producing additive manufacturing dispersions and parts thereof.

In one embodiment the composition of this invention comprises an Additive Manufacturing dispersion, wherein the dispersion comprises at least one portion of a cross-linkable moiety, and oxidized, discrete carbon nanotubes with a bonded dispersing agent on at least one sidewall of the oxidized discrete carbon nanotubes wherein the oxidized, discrete carbon nanotubes are present in the range of greater than zero and up to about 30% by weight based on the total weight of the dispersion and a plurality of the carbon nanotubes present in the dispersion are discrete.

Preferably, the oxidized, discrete carbon nanotubes comprise an interior and exterior surface, each surface comprising an interior surface oxidized species content and an exterior surface oxidized species content, wherein the interior surface oxidized species content differs from the exterior surface oxidized species content by at least about 20%, and as high as 100%.

The oxidized discrete carbon nanotubes can comprise a mixture of oxidized discrete carbon nanotubes with a bimodal or trimodal distribution of the diameters of the oxidized discrete carbon nanotubes formed from combinations of oxidized discrete single wall, oxidized discrete double wall and oxidized discrete multiwall carbon nanotubes.

The bonded dispersing agent on the sidewall of the oxidized discrete carbon nanotubes is preferably covalently bonded.

The bonded dispersing agent on the sidewall of the oxidized discrete carbon nanotubes preferably comprises an average molecular weight in the range of about 50 to about 20,000 daltons and the weight fraction of bonded dispersing agent on the sidewall of the discrete carbon nanotubes relative to the oxidized discrete carbon nanotubes is greater than about 0.02 and less than about 0.8.

The bonded dispersing agent on the sidewall of the oxidized discrete carbon nanotubes is preferably miscible with a material in contact with the bonded dispersing agent.

A second embodiment of the invention is an Additive Manufacturing dispersion, wherein the dispersion comprises at least one portion of a cross-linkable acrylate moiety and oxidized, discrete carbon nanotubes with a bonded dispersing agent on at least one sidewall of the oxidized discrete carbon nanotubes wherein the bonded dispersing agent on the sidewall of the discrete carbon nanotubes comprises molecular units selected from the group of ethers.

The molecular units of the second embodiment preferably comprise ethylene oxide.

The first or second embodiments can further comprise fillers in the % weight from about 0.1% to about 30% by weight of the dispersion, preferably wherein the fillers are selected from the group consisting of carbon black, graphene, oxidized graphene, reduced graphene, carbon fibers, silicas, silicates, halloysite, clays, calcium carbonate, wollastonite, glass, fire-retardants and talc.

The first or second embodiments can further comprise a member of the group consisting of thermoplastics, thermosets, and elastomers.

The first or second embodiments can further comprise a core shell elastomer, wherein the elastomer preferably comprises particles having diameters from about 0.01 to about 1 micrometer.

The first or second embodiments can further comprise semi-conductor, metallic, or ceramic powders, wherein the powders comprise particle diameters from about 1 nm to about 20 micrometers.

The first or second embodiments can further comprise at least one additional dispersing agent attached to the sidewall of the oxidized discrete carbon nanotubes selected from the group consisting of anionic, cationic, nonionic and zwitterionic surfactants, polyvinyl alcohols, copolymers of polyvinyl alcohols and polyvinyl acetates, polyvinylpyrrolidones and their copolymers, carboxymethyl cellulose, carboxypropyl cellulose, carboxymethyl propyl cellulose, hydroxyethyl cellulose, polyetherimines, polyethers, starch, and mixtures thereof.

The first or second embodiments wherein the oxidized discrete carbon nanotubes comprise about 0.1% to about 20% by weight of nitrogen atoms.

A third embodiment of the Invention is an Additive Manufacturing dispersion wherein the dispersion comprises at least one portion of a thermoplastic moiety and discrete carbon nanotubes with a bonded dispersing agent on at least one sidewall of the discrete carbon nanotubes wherein the discrete carbon nanotubes are present in an amount greater than zero and up to about 30% by weight based on the total weight of the dispersion.

The third embodiment can comprise a bonded dispersing agent on the sidewall of the oxidized discrete carbon nanotubes at least partially thermally decomposes at less than about 500° C. in nitrogen with less than about 5% weight ash content.

The third embodiment can comprise a plurality of discrete carbon nanotubes.

Any of the three embodiments can comprise a part made by Additive Manufacturing having an electrical resistance less than about 10 billion ohms per square.

Any of the three embodiments can comprise a dispersion having a UV-visible absorption at 500 nm greater than about 0.5 units of absorbance for a concentration of oxidized discrete carbon nanotubes in the dispersion of $2.5 \times 10^{-5}$ g/ml.

Any of the three embodiments can further comprise a filler selected from the group of thermally conducting materials, such as but not limited to metals and metal alloys, boron nitride, aluminum oxide, silicon nitride, aluminum nitride, diamond, graphite and graphene.

Any of the three embodiments can further comprise a biologically reactive species selected from the group consisting of species that can interact with bacteria, virus, fungi, and biological agents.

Oxidized carbon nanotubes are those carbon nanotubes that have been subjected to oxidizing media, such as but not limited to, concentrated nitric acid, peroxides and persulfates, that introduces chemical units such as carboxylic acids, hydroxyls, ketones and lactones. The oxidized discrete carbon nanotubes are selected from the group consisting of oxidized discrete single wall, oxidized discrete double wall, or oxidized discrete multiwall carbon nanotubes.

The oxidized, discrete carbon nanotubes can also comprise an interior and exterior surface, each surface comprising an interior surface oxidized species content (also called interior oxygen containing species content because the interior oxygen species may differ from the exterior oxygen species) and an exterior surface oxidized species content (also called exterior oxygen containing species content because the interior oxygen species may differ from the exterior oxygen species), wherein the interior surface oxidized species content differs from the exterior surface oxidized species content by at least 20%, and as high as 100%, preferably wherein the interior surface oxidized species content is less than the exterior surface oxidized species content. The interior surface oxidized species content can be up to 3 weight percent relative to carbon nanotube weight, preferably from about 0.01 to about 3 weight percent relative to carbon nanotube weight, more preferably from about 0.01 to about 2, most preferably from about 0.01 to about 1. Especially preferred interior surface oxidized species content is from zero to about 0.01 weight percent relative to carbon nanotube weight. The exterior surface oxidized species content can be from about 0.1 to about 65 weight percent relative to carbon nanotube weight, preferably from about 1 to about 40, more preferably from about 1 to about 20 weight percent relative to carbon nanotube weight. This is determined by comparing the exterior oxidized species content for a given plurality of nanotubes against the total weight of that plurality of nanotubes.

The oxidized, discrete carbon nanotubes can further comprise a mixture of oxidized discrete carbon nanotubes with a bimodal or trimodal distribution of the diameters of the oxidized discrete carbon nanotube formed from combinations of oxidized discrete single wall, oxidized discrete double wall and oxidized discrete multiwall carbon nanotubes. Preferably, the dispersion of oxidized discrete carbon nanotubes comprises a majority of oxidized discrete multiwall carbon nanotubes, more preferably a majority of oxidized discrete double wall carbon nanotubes and even more preferably a majority of oxidized discrete single wall carbon nanotubes. The meaning of majority is more than 50% by weight of all the carbon nanotubes present in the dispersion.

In another embodiment of this invention the Additive Manufacturing dispersion the bonded dispersing agent on the sidewall of the oxidized discrete carbon nanotubes is hydrogen bonded, preferably ionically bonded and more preferably covalently bonded.

In another embodiment the oxidized discrete carbon nanotubes further have a bonded dispersing agent on the sidewall of the oxidized discrete carbon nanotubes consisting of a molecular weight in the range of about 50 to about 20,000 daltons. Preferably the molecular weight range of the bonded dispersing agent is from about 60 to about 5000 daltons and more preferably from about 70 to about 1000 daltons. The bonded dispersing agent on the sidewall of the oxidized discrete carbon nanotubes consists of chemical units selected from the group of carbon-carbon bonds, carbon-nitrogen bonds, carbon-oxygen bonds, carbon-sulfur bonds and silicon-oxygen bonds. In the presence of crosslinkable matrices the chemical units of the bonded dispersing agent are preferred to be able to be crosslinked into the matrices.

The weight fraction of bonded dispersing agent on the sidewall of the discrete carbon nanotubes relative to the oxidized discrete carbon nanotubes is greater than about 0.02 and less than about 0.8. Preferably the weight fraction of bonded dispersing agent from about 0.03 to about 0.6, more preferably from about 0.05 to about 0.5 and most preferably from about 0.06 to about 0.4.

The bonded dispersing agent on the sidewall of the oxidized discrete carbon nanotubes is selected such that it has good compatibility with a material in contact with the dispersing agent. Good compatibility here is to mean a sufficient amount of electronic, van der Waals, ionic or dipole interactions such that the oxidized carbon nanotube can be dispersed as individual or discrete carbon nanotubes. Preferably the bonded dispersing agent on the sidewall of the oxidized discrete carbon nanotubes is selected such that it is thermodynamically miscible, i.e., forms a homogeneous mixture with a material in contact with the dispersing agent.

The bonded dispersing agent on the sidewall of the discrete carbon nanotubes can further comprise ethylene oxide molecular units. More preferred is the bonded dispersion agent comprise a mixture of propylene oxide and ethylene oxide molecular units. There may be a mixture of bonded dispersing agents on the sidewall of the discrete carbon nanotubes or a mixture of oxidized discrete carbon nanotubes with different types of bonded dispersion agents.

In another embodiment of this invention the bonded dispersing agent on the sidewall of the oxidized discrete carbon nanotubes may be further selected to have a thermal decomposition such that at less than 500° C. in nitrogen there is less than about 5% weight ash content of the dispersing agent. Preferably the bonded dispersing agent on the sidewall of the oxidized discrete carbon nanotubes has a thermal decomposition such that at less than about 500° C. in nitrogen there is less than about 1% weight ash content of the dispersing agent and more preferably the bonded dispersing agent on the sidewall of the oxidized discrete carbon nanotubes has a thermal decomposition such that at less than about 400° C. in nitrogen there is less than about 1% weight ash content of the dispersing agent.

The oxidized discrete carbon nanotubes with a bonded dispersing agent on the sidewall of the oxidized discrete carbon nanotubes consist of an aspect ratio, known as the ratio of the length to diameter of the oxidized discrete carbon nanotube, from about 10 to about 10000. For oxidized discrete single wall carbon nanotubes the aspect ratio is preferred to be from about 300 to about 10000, for oxidized discrete double wall carbon nanotubes the aspect ratio is preferred to be from about 150 to about 5000 and for oxidized discrete multiwall carbon nanotubes the aspect ratio is preferred from about 40 to about 500.

The aspect ratio of the oxidized discrete carbon nanotubes can be a unimodal distribution, or a multimodal distribution (such as a bimodal or trimodal distribution). The multimodal distributions can have evenly distributed ranges of aspect ratios (such as 50% of one L/D range and about 50% of another L/D range). The distributions can also be asymmetrical-meaning that a relatively small percent of discrete nanotubes can have a specific L/D while a greater amount can comprise another aspect ratio distribution.

An embodiment of this invention is that the oxidized discrete carbon nanotubes with a bonded dispersing agent on the sidewall of the oxidized discrete carbon nanotubes are present in the weight range greater than zero and up to about 30% by weight based on the total weight of the dispersion. Preferably the weight range of oxidized discrete carbon nanotubes with a bonded dispersing agent on the sidewall of the oxidized discrete carbon nanotubes present in the dispersion is from about 0.01 to about 10% by weight and more preferably from about 0.01 to about 5% by weight based on the total weight of the dispersion.

In yet another embodiment of this invention is that a plurality of the carbon nanotubes present in the dispersion are discrete. Preferably at least about 51% by weight of oxidized carbon nanotubes with a bonded dispersing agent on the sidewall of the oxidized carbon nanotubes present in the dispersion are discrete, preferably at least about 65% by weight of oxidized carbon nanotubes with a bonded dispersing agent on the sidewall of the oxidized carbon nanotubes present in the dispersion are discrete, more preferably at least about 75% by weight of oxidized carbon nanotubes with a bonded dispersing agent on the sidewall of the oxidized carbon nanotubes present in the dispersion are discrete and most preferably at least about 85% by weight of carbon nanotubes present in the dispersion are discrete.

In another embodiment of this invention the dispersion of oxidized discrete carbon nanotubes with a bonded dispersing agent on the sidewall of the oxidized discrete carbon nanotubes comprises fillers in the % weight from about 0.05% to about 80% relative to the total weight of the dispersion. Preferably the % weight of fillers is from about 0.05% to about 30% and most preferably from about 0.1% to about 10% relative to the total weight of the dispersion.

The fillers are selected from the group consisting of carbon black, graphene, oxidized graphene, reduced graphene, carbon fibers, silicas, silicates, halloysite, clays, calcium carbonate, wollastonite, glass, flame retardants and talc. The fillers may be in the shapes of roughly spherical particles, rods, fibers or plates. Preferably the fillers have at least one scale of dimension greater than about 1 nm and less than about 10 micrometers, more preferably have at least one scale of dimension greater than about 5 nm and less than about 2 micrometers and most preferably have at least one scale of dimension greater than about 10 nm and less than about 1 micrometer.

In some embodiments the dispersion comprising of oxidized discrete carbon nanotubes further comprises a mixture of at least two different fillers. In some embodiments the dispersion comprising oxidized discrete carbon nanotubes further comprises a mixture of a different species of a single filler which may vary by particles size, thermal conductivity, packing, or molecular weight.

In further embodiments of this invention the dispersion further comprises photo-crosslinkable monomers, oligomers or polymers. The cross-linkable monomers, oligomers or polymers contain molecular units selected from the group of carbon-carbon double bonds, carbon-carbon triple bonds, urethanes, acrylates, alkylacrylates, cyanonitriles, cyanoacrylates, nitriles, epoxies, amides, amines, alcohols, ethers and esters.

In another embodiment the dispersion of the oxidized discrete carbon nanotubes with a bonded dispersing agent on the sidewall of the oxidized discrete carbon nanotubes further comprises a thermoplastic. The dispersion of oxidized discrete carbon nanotubes with a bonded dispersing agent on the sidewall of the oxidized discrete carbon nanotubes may coat the thermoplastic or oxidized discrete carbon nanotubes with a bonded dispersing agent on the sidewall of the oxidized discrete carbon nanotubes may be dispersed within the thermoplastic. A preferred thermoplastic is selected from the group of amorphous and semi-crystalline thermoplastics, including, but not limited to, Polylactic acid (PLA), Acrylonitrile butadiene styrene (ABS), Polycarbonate (PC), Polycarbonate-Acrylonitrile butadiene styrene blend (PC-ABS), Polyetherimide (PEI), Polyphenylsulfone (PPSF), Polyethylene terephthalate (PET), Polyethylene terephthalate glycol (PETG), Polyether ether ketone (PEEK), Polyamides, such as but not limited to Nylon 12, Nylon 11, Nylon 6, and Nylon 6,6, polyvinyl alcohol and copolymers, polyvinylbutyrate and copolymers, polyvinylpyrrolidone and copolymers, polyether and copolymers. The thermoplastic may be a linear, grafted, comb or block polymer.

In yet another embodiment of this invention the dispersion of the oxidized discrete carbon nanotubes with a bonded dispersing agent on the sidewall of the oxidized discrete carbon nanotubes further comprises elastomers. The elastomers can be selected from the group consisting of, but not limited to, natural rubber, polyisobutylene, polybutadiene, styrene-butadiene, hydrogenated styrene-butadiene, butyl rubber, polyisoprene, styrene-isoprene rubber, ethylene propylene diene, silicones, polyurethanes, polyester, polyether, polyacrylates, hydrogenated and non-hydrogenated nitrile rubbers, halogen modified elastomers, polyolefin elastomers fluoroelastomers, and combinations thereof. The elastomers may be non-crosslinked or crosslinked, grafted or copolymers.

In another embodiment the dispersion of the oxidized discrete carbon nanotubes with a bonded dispersing agent on the sidewall of the oxidized discrete carbon nanotubes further comprises polymeric impact modifiers with a glass transition temperature of less than about 25° C. The impact modifiers are selected from the group of polyethers, polyesters, vinylpolymers, polyvinylcopolymers, polyolefins polyacrylates, polyurethanes, polyamides and polysiloxanes, blends and copolymers thereof. They may be further functionalized with reactive groups, such as but not limited to epoxy, hydroxyl, isocyanate, and carboxylic groups.

The impact modifiers are preferred to be phase-separated from the main matrix material of the dispersion yet have good cohesion or thermodynamic interaction. More preferred is that the composition of the impact modifiers that are block copolymers or core-shell polymers. Examples of core shell polymers are PARALOID™ Impact Modifiers which are acrylate or butadiene based. More preferred is that the impact modifiers have a refractive index value at least within 0.03 units of the refractive index value of the matrix, more preferably within 0.02 units, so as to minimize the scattering of radiation in the UV-visible wavelength range.

The core-shell particles can include more than one core and/or more than one shell. In addition, mixtures of core-shell particles with elastomer particles can be used. In an embodiment, two different diameters of impact modifiers are used in a certain ratio. The use of two different impact modifiers with different diameters has the effect of lowering the viscosity of the liquid radiation curable resin. In an embodiment, the composition of impact modifiers is about a 7 to 1 ratio of diameter (e.g. 140 nm particles vs. a 20 nm particles) and about a 4 to 1 ratio of wt %. In another embodiment, the composition of impact modifiers is about a 5 to 1 ratio of diameter and about a 4 to 1 ratio of wt %. In another embodiment the composition of impact modifiers is about a 5 to 1 ratio of diameter and about a 6 to 1 ratio of wt %.

The phase-separated domain size of the impact modifier in the dispersion of the oxidized discrete carbon nanotubes with a bonded dispersing agent on the sidewall of the oxidized discrete carbon nanotubes can be greater than about 0.005 micrometers and less than about 1 micrometer in diameter, preferably greater than 0.01 micrometers and less than about 0.8 micrometer in diameter and most preferably greater than about 0.05 micrometers and less than about 0.6 micrometer in diameter.

The impact modifier may be present in the dispersion of the oxidized discrete carbon nanotubes with a bonded dispersing agent on the sidewall of the oxidized discrete carbon nanotubes from at least about 0.1% to less than about 30% by weight of the dispersion, preferably at least greater than about 0.5% to less than about 15% and most preferably at least about 2% to less than about 10%.

In another embodiment the dispersion of the oxidized discrete carbon nanotubes with a bonded dispersing agent on the sidewall of the oxidized discrete carbon nanotubes further comprises metallic powders. The metallic powders can contain any of those metal elements listed in the Periodic Table of Elements. The metals may also be in the form of metal oxides, carbides, silicides or nitrides, or alloys with other elements. Preferred metallic powders can be selected, but not limited to, the class of stainless steel, Inconel, bronze, copper, silver, platinum, tungsten, Aluminum, cobalt, platinum, and tungsten carbide. More preferred is that the metallic powders have a particle diameter greater than about 1 nm and less than about 20 micrometers. For more effective sintering it may be further preferred to have a bimodal metallic powder particle diameter distribution. Yet further preferred is that in the metallic powder particle distribution the number of larger particle size be in the majority.

In another embodiment the dispersion of the oxidized discrete carbon nanotubes with a bonded dispersing agent on the sidewall of the oxidized discrete carbon nanotubes further comprises ceramic powders. The ceramic powders can be selected from, but not limited to, the class of aluminum oxide, zirconium oxide, silica, boron nitride and silicon carbide and blends thereof. Preferred is that the ceramic powders have a particle diameter greater than about 1 nm and less than about 20 micrometers. For more effective sintering of the ceramic it may be further preferred to have a bimodal ceramic powder particle diameter distribution. Yet further preferred that in the ceramic powder particle distribution that the number of larger particle size be in the majority.

In another embodiment the dispersion of the oxidized discrete carbon nanotubes with a bonded dispersing agent on the sidewall of the oxidized discrete carbon nanotubes further comprises a mixture of ceramic powders and metallic powders which when sintered form cermets. The preferred cermets which are based on carbides, nitrides, borides, and silicides of the fourth to sixth element groups of the Periodic Table of Elements.

In another embodiment of this invention the dispersion of the oxidized discrete carbon nanotubes with a bonded dispersing agent on the sidewall of the oxidized discrete carbon nanotubes further comprising at least one additional dispersing agent attached to the sidewall of the oxidized discrete carbon nanotubes selected from the group consisting of anionic, cationic, nonionic and zwitterionic surfactants, polyvinyl alcohols, copolymers of polyvinyl alcohols and polyvinyl acetates, polyvinylpyrrolidones and their copolymers, carboxymethyl cellulose, carboxypropyl cellulose, carboxymethyl propyl cellulose, hydroxyethyl cellulose, polyetherimines, polyethers, starch, and mixtures thereof. Preferred are the non-covalently attached polymeric dispersion agents be selected from the group of amphiphilic polymers.

The molecular weight of the additional dispersing agent attached to the sidewall of the oxidized discrete carbon nanotubes is preferred to be in the range of about 100 to about 400,000 daltons, more preferably in the range of about 1000 to about 200,000 daltons and most preferably in the range of about 10,000 to about 100,000 daltons.

The additional dispersing agents attached to the sidewall of the oxidized discrete carbon nanotubes with a bonded dispersing agent on the sidewall of the oxidized discrete carbon nanotubes can be present in the dispersion in the weight ratio of attached additional dispersing agent to oxidized discrete carbon nanotubes with a bonded dispersing agent on the sidewall of the oxidized discrete carbon nanotubes from about 0.01 to about 2. Preferably the weight ratio is from about 0.1 to about 1 and most preferably from about 0.2 to about 0.75.

Another embodiment of this invention is that the dispersion of the oxidized discrete carbon nanotubes with a bonded dispersing agent on the sidewall of the oxidized discrete carbon nanotubes further comprises an organic solvent. A preferred organic solvent is selected from the group of alcohols, ethers, ketones, dioxolane, acetates, glycols, and mixtures thereof.

Yet another embodiment of this invention is that the dispersion of the oxidized discrete carbon nanotubes with a bonded dispersing agent on the sidewall of the oxidized discrete carbon nanotubes further comprises water.

In an embodiment of this invention the dispersion of the oxidized discrete carbon nanotubes with a bonded dispersing agent on the sidewall of the oxidized discrete carbon nanotubes is electrostatic-dissipative. Preferably the dispersion has a surface resistivity of less than 10 billion ohms per square, more preferably less than 10 million ohms per square.

In yet another embodiment of this invention the dispersion of the oxidized discrete carbon nanotubes with a bonded dispersing agent on the sidewall of the oxidized discrete carbon nanotubes further comprises about 0.1% to about 20% by weight of nitrogen atoms.

In one embodiment of this invention the UV-visible absorption at 500 nm for the dispersion of the oxidized discrete carbon nanotubes with a bonded dispersing agent on the sidewall of the oxidized discrete carbon nanotubes is above 0.5 units of absorbance for a concentration of oxidized discrete carbon nanotubes with a bonded dispersing agent in the dispersion of $2.5 \times 10^{-5}$ g/ml. Preferably the unit of absorption is above 0.75 at the same concentration of oxidized carbon nanotubes and wavelength of measurement, most preferably above 1 unit of absorbance at the same concentration of oxidized carbon nanotubes and wavelength of measurement.

In yet another embodiment of this invention the filler can be selected from the group of fire retardants consisting of char formation agents, intumescent agents, and reactions in the gas phase such but not limited to organic halides (haloalkanes).

In one embodiment the dispersion of the oxidized discrete carbon nanotubes with a bonded dispersing agent on the sidewall of the oxidized discrete carbon nanotubes comprises a filler selected from the group of thermally conducting materials such as but not limited to metals and metal alloys, boron nitride, aluminum oxide, silicon nitride, aluminum nitride, diamond, graphite.

In another embodiment the dispersion of the oxidized discrete carbon nanotubes with a bonded dispersing agent on the sidewall of the oxidized discrete carbon nanotubes comprises a filler selected from the group of magnetic and ferromagnetic materials, such as but not limited to those materials containing atoms of nickel, iron, cobalt and their alloys and oxides.

An embodiment of this invention is the dispersion of the oxidized discrete carbon nanotubes with a bonded dispersing agent further comprising magnetic or ferromagnetic particles provide electromagnetic absorbance or shielding at frequencies greater than about 1 MHz, preferably at frequencies greater than about 1 GHz. The dispersion of the oxidized discrete carbon nanotubes with a bonded dispersing agent further comprising electron conducting filler particles are also desirable for shielding of radio frequencies.

In yet another embodiment the dispersion comprising at least one portion of a cross-linkable moiety, and oxidized, discrete carbon nanotubes with a bonded dispersing agent on at least one sidewall of the oxidized discrete carbon nanotubes is crosslinked at least partially by radiation followed by post-curing comprises at least one portion of a cross-linkable moiety, and oxidized, discrete carbon nanotubes with a bonded dispersing agent on at least one sidewall of the oxidized discrete carbon nanotubes to achieve final desired part performance by thermal or irradiative methods wherein the time to post cure to achieve the final desired part performance is 10% less than the dispersion without oxidized discrete carbon nanotubes, preferably 25% less time and more preferably 50% less time.

In another embodiment the dispersion comprising at least one portion of a cross-linkable moiety, and oxidized, discrete carbon nanotubes with a bonded dispersing agent on at least one sidewall of the oxidized discrete carbon nanotubes is jettable.

In another embodiment the dispersion comprising at least one portion of a cross-linkable moiety, and oxidized, discrete carbon nanotubes with a bonded dispersing agent on at least one sidewall of the oxidized discrete carbon nanotubes further comprising materials which can be sintered using about 10% less radiation power than a similar dispersion not containing oxidized discrete carbon nanotubes, preferably using about 25% less radiation power, more preferably using about 50% less radiation power than a similar dispersion not containing oxidized discrete carbon nanotubes.

In one embodiment the dispersion of oxidized discrete carbon nanotubes with bonded dispersion agent further comprises an elastomer wherein the final part exhibits at least about 20% higher resistance to fracture under cyclic fatigue, preferably at least about 50% and most preferably at least about 100% higher resistance to fracture than a similar dispersion without the oxidized discrete carbon nanotubes with bonded dispersion agent.

OTHER EMBODIMENTS

Embodiment 1. An Additive Manufacturing dispersion wherein the dispersion comprises at least one portion of a cross-linkable moiety, and oxidized, discrete carbon nanotubes with a bonded dispersing agent on at least one sidewall of the oxidized discrete carbon nanotubes wherein the oxidized, discrete carbon nanotubes are present in the range of greater than zero and up to about 30% by weight based on the total weight of the dispersion and a plurality of the carbon nanotubes present in the dispersion are discrete.

Embodiment 2. The dispersion of Embodiment 1 wherein the oxidized, discrete carbon nanotubes comprise an interior and exterior surface, each surface comprising an interior surface oxidized species content and an exterior surface oxidized species content, wherein the interior surface oxidized species content differs from the exterior surface oxidized species content by at least about 20%, and as high as 100%.

Embodiment 3. The dispersion of Embodiment 1 wherein the oxidized discrete carbon nanotubes comprise a mixture of oxidized discrete carbon nanotubes with a bimodal or trimodal distribution of the diameters of the oxidized discrete carbon nanotubes formed from combinations of oxidized discrete single wall, oxidized discrete double wall and oxidized discrete multiwall carbon nanotubes.

Embodiment 4. The dispersion of Embodiment 1 wherein the bonded dispersing agent on the sidewall of the oxidized discrete carbon nanotubes is covalently bonded.

Embodiment 5. The dispersion of Embodiment 1 wherein the bonded dispersing agent on the sidewall of the oxidized discrete carbon nanotubes comprises an average molecular weight in the range of about 50 to about 20,000 daltons and the weight fraction of bonded dispersing agent on the sidewall of the discrete carbon nanotubes relative to the oxidized discrete carbon nanotubes is greater than about 0.02 and less than about 0.8.

Embodiment 6. The dispersion of Embodiment 1 wherein the bonded dispersing agent on the sidewall of the oxidized discrete carbon nanotubes is miscible with a material in contact with the bonded dispersing agent.

Embodiment 7. An Additive Manufacturing dispersion wherein the dispersion comprises at least one portion of a cross-linkable acrylate moiety and oxidized, discrete carbon nanotubes with a bonded dispersing agent on at least one sidewall of the oxidized discrete carbon nanotubes wherein the bonded dispersing agent on the sidewall of the discrete carbon nanotubes comprises molecular units selected from the group of ethers.

Embodiment 8. The dispersion of Embodiment 7 wherein the molecular units comprise ethylene oxide.

Embodiment 9. The dispersion of Embodiment 1 further comprising fillers in the % weight from about 0.1% to about 30% by weight of the dispersion selected from the group consisting of carbon black, graphene, oxidized graphene, reduced graphene, carbon fibers, silicas, silicates, halloysite, clays, calcium carbonate, wollastonite, glass, fire-retardants and talc.

Embodiment 10. The dispersion of Embodiment 1 further comprising a member of the group consisting of thermoplastics, thermosets, and elastomers.

Embodiment 11. The dispersion of Embodiment 1 further comprising a core shell elastomer further comprising particles diameters from about 0.01 to about 1 micrometer.

Embodiment 12. The dispersion of Embodiment 1 further comprising semi-conductor, metallic and, or ceramic powders with particle diameters from about 1 nm to about 20 micrometers.

Embodiment 13. The dispersion of Embodiment 1 further comprising at least one additional dispersing agent attached to the sidewall of the oxidized discrete carbon nanotubes selected from the group consisting of anionic, cationic, nonionic and zwitterionic surfactants, polyvinyl alcohols, copolymers of polyvinyl alcohols and polyvinyl acetates, polyvinylpyrrolidones and their copolymers, carboxymethyl cellulose, carboxypropyl cellulose, carboxymethyl propyl cellulose, hydroxyethyl cellulose, polyetherimines, polyethers, starch, and mixtures thereof.

Embodiment 14. The composition of Embodiment 1 wherein the oxidized discrete carbon nanotubes comprise about 0.1% to about 20% by weight of nitrogen atoms.

Embodiment 15. An Additive Manufacturing dispersion wherein the dispersion comprises at least one portion of a thermoplastic moiety and discrete carbon nanotubes with a bonded dispersing agent on at least one sidewall of the discrete carbon nanotubes wherein the discrete carbon nanotubes are present in an amount greater than zero and up to about 30% by weight based on the total weight of the dispersion.

Embodiment 16. The dispersion of Embodiment 15 wherein a bonded dispersing agent on the sidewall of the oxidized discrete carbon nanotubes at least partially thermally decomposes at less than about 500° C. in nitrogen with less than about 5% weight ash content.

Embodiment 17. The Additive Manufacturing dispersion of Embodiment 15 wherein a plurality of carbon nanotubes is discrete.

Embodiment 18. The dispersion of Embodiment 1 wherein a part made by Additive Manufacturing has an electrical resistance less than 10 billion ohms per square.

Embodiment 19. The dispersion of Embodiment 1 wherein the dispersion has a UV-visible absorption at 500 nm greater than about 0.5 units of absorbance for a concentration of oxidized discrete carbon nanotubes in the dispersion of $2.5 \times 10-5$ g/ml.

Embodiment 20. The dispersion of Embodiment 1 further comprises a filler selected from the group of thermally conducting materials, such as but not limited to metals and metal alloys, boron nitride, aluminum oxide, silicon nitride, aluminum nitride, diamond, graphite and graphene.

Embodiment 21. An additive manufacturing dispersion for at least partially encapsulating electronic components, wherein the dispersion comprises:
at least one portion of a cross-linkable moiety; and
oxidized, discrete carbon nanotubes;
wherein the oxidized, discrete carbon nanotubes comprise a dispersing agent bonded on a sidewall of the oxidized, discrete carbon nanotubes; and
wherein the oxidized, discrete carbon nanotubes are present in the range of greater than zero and up to about 30% by weight based on the total weight of the dispersion; and
wherein a plurality of the carbon nanotubes present in the dispersion are discrete.

DETAILED DESCRIPTION OF THE INVENTION

In the following description, certain details are set forth such as specific quantities, sizes, etc., so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

In various embodiments a dispersion is disclosed comprising oxidized, discrete carbon nanotubes with a bonded dispersing agent on the sidewall of the oxidized discrete carbon nanotubes wherein the oxidized, discrete carbon nanotubes are present in an amount greater than zero and up to about 30% by weight based on the total weight of the dispersion and a plurality of the oxidized carbon nanotubes present in the dispersion are discrete.

As-made carbon nanotubes using metal catalysts such as iron, aluminum or cobalt can retain a significant amount of the catalyst associated or entrapped within the carbon nanotube, as much as five weight percent or more. These residual metals can be deleterious in such applications as electronic devices because of enhanced corrosion or can interfere with the vulcanization process in curing elastomer composites. Furthermore, these divalent or multivalent metal ions can associate with carboxylic acid groups on the carbon nanotube and interfere with the discretization of the carbon nanotubes in subsequent dispersion processes. In an embodiment a dispersion is disclosed comprising oxidized, discrete carbon nanotubes with a bonded dispersing agent on the sidewall of the oxidized discrete carbon nanotubes comprising a residual metal concentration of less than about 50,000 parts per million, ppm, and preferably less than about 10,000 parts per million. The residual catalyst concentration can be conveniently determined by using thermogravimetry by heating at 5° C./min in nitrogen from 25° C. to 800° C. then switching the gas to air and holding at 800° C. for 30 minutes. The % residual ash is determined by the weight of material remaining compared to the weight of the starting material. The ash can then be analyzed for metal type using energy dispersive X-ray and a scanning electron microscope. Alternatively, the oxidized discrete carbon nanotubes can be separation from the dispersion medium and analyzed using atomic absorption techniques.

The oxidation level of the oxidized discrete carbon nanotubes is defined as the amount by weight of oxygenated species covalently bound to the carbon nanotube. The thermogravimetric method for the determination of the percent weight of oxygenated species on the carbon nanotube involves taking about 5 mg of the dried oxidized carbon nanotube and heating at 5° C./minute from room temperature to 800 degrees centigrade in a dry nitrogen atmosphere. The percentage weight loss from 200 to 600 degrees centigrade is taken as the percent weight loss of oxygenated species. The oxygenated species can also be quantified using Fourier transform infra-red spectroscopy, FTIR, particularly in the wavelength range from 1680 to 1730 cm-1.

The oxidized carbon nanotubes can have oxidation species comprising of carboxylic acid or derivative carbonyl containing species. The derivative carbonyl species can include ketones, quaternary amines, amides, esters, acyl halogens, monovalent metal salts and the like. Alternatively, or in addition, the carbon nanotubes may comprise an oxidation species selected from hydroxyl or derived from hydroxyl containing species, ketones and lactones.

The term discrete, alternatively known by the term exfoliated, is taken here to mean individual carbon nanotubes separated substantially along their length, i.e., not bundled. Aspect ratio is defined as the length to diameter ratio of the carbon nanotube. If a bundle of carbon nanotubes are present the aspect ratio is taken as the length to diameter ratio of the bundle. For a spherical ball of entangled carbon nanotubes the aspect ratio is taken as 1.

Based on the desired application the aspect ratio of the oxidized discrete carbon nanotubes can be a unimodal distribution, or a multimodal distribution (such as a bimodal or trimodal distribution). The multimodal distributions can have evenly distributed ranges of aspect ratios (such as 50% of one L/D range and about 50% of another L/D range). The distributions can also be asymmetrical-meaning that a relatively small percent of discrete nanotubes can have a specific L/D while a greater amount can comprise another aspect ratio distribution. The aspect ratio of the oxidized discrete carbon nanotubes can be determined, for example, using dilutions of the dispersion in organic solvent and scanning electron microscopy.

Manufacturers of carbon nanotubes that may be suitable for use in the applications described herein include, for example, Southwest Nanotechnologies, Zeonano or Zeon, CNano Technology, Nanocyl, ACS Materials, American Elements, Chasm Technologies, Haoxin Technology, Hanwha Nanotech Group, Hyperion Catalysis, KH Chemical, Klean Commodities, LG Chem, Nano-C, NTP Shenzhen Nanotech Port, Nikkiso, Raymor, Saratoga Energy, SK Global, Solid Carbon Products, Sigma Aldrich, Sun Nanotech, Thomas Swan, TimesNano, Tokyo Chemical Industry, XF Nano, and OCSiAl.

A method to obtain discrete carbon nanotubes is to subject the carbon nanotubes to high mechanical forces. During shearing, samples may be subjected to intensely disruptive forces generated by shear (turbulent) and/or cavitation with process equipment capable of producing energy densities as high as of $10^6$ to $10^8$ Joules/m$^3$. Equipment that meets this specification includes but is not limited to ultrasonicators, cavitators, mechanical homogenizers, pressure homogenizers and microfluidizers. One such homogenizer is shown in U.S. Pat. No. 756,953, the disclosure of which is incorporated herein by reference. Additional shearing equipment includes, but is not limited to, HAAKE™ mixers, Brabender mixers, Omni mixers, Silverson mixers, Colloidal mills, Gaullin homogenizers, and/or twin-screw extruders. After shear processing, the carbon nanotubes bundles have been loosened, thereby exposing the surface of a greater number of nanotubes and/or a greater portion of the surface of the nanotubes to the surrounding environment. Typically, based on a given starting amount of entangled as-received and as-made carbon nanotubes, a plurality of high-surface area oxidized carbon nanotubes results from this process, preferably at least about 60%, more preferably at least about 75%, most preferably at least about 95% and as high as 100%, with the minority of the tubes, usually the vast minority of the tubes remaining tightly bundled and with the surface of such tightly bundled nanotubes substantially inaccessible.

Bosnyak et al., in various patent applications (e.g., US 2012-0183770 A1 and US 2011-0294013 A1), have made discrete carbon nanotubes through judicious and substantially simultaneous use of oxidation and shear forces, thereby oxidizing both the inner and outer surface of the nanotubes, typically to approximately the same oxidation level on the inner and outer surfaces, resulting in individual or discrete tubes.

In many embodiments, the present inventions differ from those earlier Bosnyak et al. applications and disclosures. In the process of oxidizing the carbon nanotubes and bonding the dispersing agent on the sidewall of the oxidized discrete carbon nanotubes, the degree of fibrillation of the carbon nanotubes can influence the population of carbon nanotubes that differ by extent or type of oxygen containing species and also the bonded dispersing agent on the sidewall of the oxidized carbon nanotubes. For example, if many of the tubes are aligned as trunks then the tubes within the core of the trunk are less likely to contain oxygenated species on reaction with say nitric acid than the tubes on the outermost portion of the trunk. For a more homogeneous population of modified carbon nanotubes it is desired to have discrete or open structure of carbon nanotubes during the reaction to modify the carbon nanotube. For some applications such as, but not limited to electrical conductivity in biphasic materials it may be desirable to control the degree of fibrillation of the carbon nanotube bundle to obtain a distribution of bonded dispersing agent on the sidewall of the oxidized discrete carbon nanotubes.

The dispersion comprising oxidized discrete carbon nanotubes with a bonded dispersing agent on the sidewall of the oxidized discrete carbon nanotubes can be made by first making oxidized discrete carbon nanotubes then bonding the dispersing agent on the sidewall or ends of the oxidized discrete carbon nanotubes, or alternatively making oxidized carbon nanotubes, then bonding the dispersing agent on the sidewall or ends of the oxidized carbon nanotubes, then making the carbon nanotubes with bonded dispersion agent discrete.

Although not limited by the chemistry of covalently bonding dispersion agents to the carbon nanotubes, it is convent to use the carboxylic acid groups on the carbon nanotubes to react with amine functional groups of the selected dispersion agent. Examples, but not limited by, of suitable dispersion agents are commercial products from Huntsman Corporation which are amine terminated polyethers, Jeffamine. The Jeffamine series can differ in their propylene oxide to ethylene oxide ratio as well as the degree of amination. Alternatively, hydroxyl groups present on the carbon nanotubes can be reacted with carboxyl, isocyanate, or glycidyl groups of the selected dispersion agent. Other useful chemical moieties for covalently bonding molecules to the sidewall of carbon nanotubes include, but not limited to, azides, acyl halides and silane moieties.

The dispersion of oxidized discrete carbon nanotubes with bonded dispersion agent can be used advantageously in Additive Manufacturing to improve the processing and part performance by employing near infra-red to radio frequency radiation up to 1 Terahertz which is absorbed rapidly by the carbon nanotubes to create heat. This effect can be used to improve the time required to fully cure cross-linkable molecules, improve the sintering of materials and reduced part warpage.

Examples of suitable impact modifiers are elastomers and, more preferably, prefabricated elastomer particles. These elastomers have a glass transition temperature (Tg) lower than 0° C., preferably lower than −20° C.

Particle size of the impact modifying component can be accomplished by using, for example, a dynamic light scattering nanoparticle size analysis system. An example of such a system is the LB-550 machine, available from Horiba Instruments, Inc. A preferred method of measuring particle size is laser diffraction particle size analysis in accordance with ISO13320:2009. Information regarding such analysis can be found in Setting New Standards for Laser Diffraction Particle Size Analysis. Alan Rawle and Paul Kippax, Laboratory Instrumentation News, Jan. 21, 2010.

Monomers from a liquid radiation curable resin or solvents used in analysis can affect the measured average particle size. Additionally, analysis by laser diffraction may require the use of a solvent or other low viscosity dispersant. These solvents may affect measured average particle size. For the purposes of this work, dispersed average particle size refers to those particles that have been exposed to the listed monomers of a given formulation, dispersed, and then analyzed using propylene carbonate as solvent for laser diffraction particle size analysis. Dispersions of impact modifier particles were subjected to particle size analysis while in dilute propylene carbonate solution, typically used was a concentration of 0.1-0.4 g dispersion in 10 g propylene carbonate.

Suitable impact modifying components, which can be mixed into the dispersion of oxidized discrete carbon nanotubes with bonded dispersion agent are elastomers based on copolymers of ethylene or propylene and one or more $C_2$ to $C_{12}$ olefin monomers.

Examples of such are ethylene/propylene copolymers or ethylene/propylene copolymers, optionally containing a third copolymerizable diene monomer (EPDM), such as 1,4-hexadiene, dicyclopentadiene, di-cyclooctadiene, methylene norbornene, ethylidene norbornene and tetrahydroindene; ethylene/α-olefin copolymers, such as ethylene-octene copolymers and ethylene/α-olefin/polyene copolymers.

Other suitable elastomers are polybutadiene, polyisoprene, styrene/butadiene random copolymer, styrene/isoprene random copolymer, acrylic rubbers (e.g., polybutylacrylate), poly (hexamethylene carbonate), ethylene/acrylate random copolymers and acrylic block copolymers, styrene/butadiene/(meth)acrylate (SBM) block-copolymers, styrene/butadiene block copolymer (styrene-butadiene-styrene block copolymer (SBS), styrene-isoprene-styrene block copolymer (SIS) and their hydrogenated versions, SEBS, SEPS), and (SIS) and ionomers.

Suitable commercial elastomers are Kraton (SBS, SEBS, SIS, SEBS and SEPS) block copolymers produced by Shell, Nanostrength block copolymers E20, E40 (SBM type) and M22 (full-acrylic) as produced by Arkema, Lotryl ethyl/acrylate random copolymer (Arkema) and Surlyn ionomers (Dupont).

Optionally, the elastomer may be modified to contain reactive groups such as e.g. epoxy, oxetane, carboxyl or alcohol. This modification can e.g. be introduced by reactive grafting or by copolymerization. Commercial examples of the latter are the Lotader random ethylene/acrylate copolymers AX8840 (glycidyl methacrylate/GMA modified), AX8900 and AX8930 (GMA and maleic anhydride modified/MA) produced by Arkema.

Optionally, the elastomer may be crosslinked after mixing into a dispersion of oxidized discrete carbon nanotubes with bonded dispersion agent. The crosslinking structure may be introduced via a conventional method. As examples of crosslinking agents used in such a materials peroxide, sulfur, cresol and the like, optionally in combination with multi-functional monomers like divinylbenzene, ethylene glycol di(meth)acrylate, diallylmaleate, triallylcyanurate, triallylisocyanurate, diallylphthalate, trimethylolpropane triacrylate, allyl methacrylate and the like can be given.

In an embodiment the impact modifiers that can be mixed into the dispersion of oxidized discrete carbon nanotubes with bonded dispersion agent are pre-fabricated elastomer particles. Elastomer particles may be prepared by a variety of means, including those obtained by isolation from latex made via emulsion polymerization, or preparation in-situ in another component of the composition.

Suitable commercial sources of such pre-fabricated elastomer particles are PB (polybutadiene) or PBA (polybutylacrylate) lattices available with varying average particle size from various producers, or lattices obtained by emulsification of EPDM, SBS, SIS or any other rubber.

Optionally, the elastomer may contain a crosslinking structure. The crosslinking structure may be introduced by a conventional method. As examples of crosslinking agents used in such a material peroxide, sulfur, cresol and the like, optionally in combination with multifunctional monomers like divinylbenzene, ethylene glycol di(meth)acrylate, diallylmaleate, triallylcyanurate, triallylisocyanurate, diallylphthalate, trimethylolpropane triacrylate, allyl methacrylate, and the like can be given.

Optionally, a shell may be present on the particles that can e.g. be introduced via grafting or during a second stage of emulsion polymerization. Examples of such particles are core-shell impact modifier particles that contain a rubber core and a glassy shell. Examples of core materials are polybutadiene, polyisoprene, acrylic rubber (e.g. polybutylacrylate rubber), styrene/butadiene random copolymer, styrene/isoprene random copolymer, or polysiloxane. Examples of shell materials or graft copolymers are (co)polymers of vinyl aromatic compounds (e.g. styrene) and vinyl cyanides (e.g. acrylonitrile) or (meth)acrylates, (e.g. methylmethacrylate).

Optionally, reactive groups can be incorporated into the shell by copolymerization, such as copolymerization with glycidyl methacrylate, or by treatment of the shell to form reactive functional groups. Suitable reactive functional groups include, but are not limited to, epoxy groups, oxetane groups, hydroxyl groups, carboxyl groups, vinyl ether groups, and/or acrylate groups.

Suitable commercially available products of these core-shell type elastomer particles are, for example but not limited to, Resinous Bond RKB (dispersions of core-shell particles in epoxy manufactured by Resinous Chemical Industries Co., Ltd.), Durastrength D400, Durastrength 400R (manufactured by Arkema Group), Paraloid EXL-2300 (non-functional shell), Paraloid EXL-2314 (epoxy functional shell), Paraloid EXL-2600, Paraloid KM 334, and Paraloid EXL 2300G. Paraloid core shell elastomers are manufactured by Dow Chemical Co., Genioperl P53, Genioperl P23, Genioperl P22 are manufactured by Wacker Chemical, Kane Ace MX products (manufactured by Kaneka).

Other examples of such elastomer particles are cross-linked polyorganosiloxane rubbers that may include dialkylsiloxane repeating units, where "alkyl" is $C_1$ to $C_6$ alkyl. Such particles may be made by the method disclosed in U.S. Pat. No. 4,853,434 to Block, incorporated in its entirety herein by reference. The particles may be modified to include reactive groups such as oxirane, glycidyl, oxetane, hydroxyl, vinyl ester, vinyl ether, or (meth)acrylate groups, or combinations thereof, preferably on the surface of the particles. Examples of polyorganosiloxane elastomer particles that are commercially available are Albidur.

EP 2240 (A), Albidur EP 2640, Albidur VE 3320, Albidur EP 5340, Albidur EP 5640, and Albiflex 296 (dispersions of particles in epoxy or vinyl ether resins, Hanse Chemie, Germany), Genioperl M41C (dispersion in epoxy, Wacker Chemical), Chemisnow MX Series and MP Series (Soken Chemical and Engineering Co.). Other materials that can be used to make the core-shell particles for use in the present invention can be found in for example: Nakamura et al, J Appl. Polym. Sci. v 33 n 3 Feb. 20, 1987 p 885-897, 1987, which discloses a core-shell material with a poly (butyl acrylate) core and poly (methyl methacrylate) shell. The shell has been treated so that it contains epoxide groups; Saija, L. M. and Uminski, M., Surface Coatings International Part B 2002 85, No.B2, June 2002, p. 149-53, which describes a core shell material with core and shell prepared from poly (methyl methacrylate-co-butyl acrylate), and treated with MMA or AMPS to produce material with carboxylic acid groups on the surface; Aerdts, A. M et al, Polymer 1997 38, No. 16, 1997, p. 4247-52, which describes a material using polystyrene, poly (methyl methacrylate) or polybutadiene as its core. An epoxidized poly (methyl methacrylate) is used for the shell. The epoxide sites are reactive sites on the shell of this material. In another embodiment, glycidyl methacrylate and methyl methacrylate are used as a co-monomer in the shell.

The core-shell particles can include more than one core and/or more than one shell. In addition, mixtures of core-shell particles with elastomer particles can be used. Two different diameters of impact modifiers can be used in a certain ratio to lower the viscosity of the dispersion comprising a cross-linkable monomer or oligomer. For example, the composition of impact modifiers can be about a 7 to 1 ratio of diameters i.e. 140 nm diameter particles vs 20 nm diameter particles and about a 4 to 1 ratio of wt %.

Another desirable feature of selection of the elastomer or impact modifier is to select a composition of the elastomer or impact modifier that has a refractive index value at least within 0.03 units of the refractive index value of the material it is dispersed in, more preferably within 0.02 units, so as to minimize the scattering of radiation in the UV-visible wavelength range. An example of such a mixture is Paraloid KM 334, refractive index 1.47, and Dymax BR-952-a urethane dimethacrylate, refractive index 1.48.

The dispersion of oxidized discrete carbon nanotubes with bonded dispersion agent further comprises fillers in the % weight from about 0.1% to about 30% by weight of the dispersion selected from the group consisting of carbon black, graphene, oxidized graphene, reduced graphene, carbon fibers, silicas, silicates, halloysite, clays, calcium carbonate, wollastonite, glass, fire-retardants and talc. The fillers can also be surface modified to improve their bonding and distribution within the dispersion. An example of a surface treatment is the use of a silane coupling agent to silica particles.

A general method to determine the thermal conductivity of the dispersion is to apply a known heat flux to a sample and once the sample's steady-state temperature is reached, the difference in temperature across the thickness of the sample is measured. After assuming one-dimensional heat flow and an isotropic medium, Fourier's Law is then used to calculate the measured thermal conductivity, Example 1—Oxidizing Tuball™ (OCSiAI)

500 grams of 67% weight nitric acid is heated to 95 degrees C. in a 1 liter glass reactor fitted with a stirrer and condensor. To the acid, 5 grams of as-received, single-walled carbon nanotubes (Tuball™) are added. The as-received fluffy carbon nanotubes have the morphology of tightly bundled tree-trunks which can be several millimeters in length and a millimeter in diameter. The mixture of acid and carbon nanotubes are mixed while the solution is kept at about 95 degrees Celsius for 5 hours. At the end of the reaction period, the oxidized single wall carbon nanotubes are filtered to remove the acid and washed with reverse osmosis (RO) water to pH of 3-4. The resulting CNTs were oxidized to about 3.6% and contained 4.4% metal residue.

Example 2—Oxidizing Multiwall Carbon Nanotubes, CNano Flotube 9000

4 liters of concentrated nitric acid containing 65% nitric acid are added into a 10 liter temperature controlled reaction vessel fitted with a sonicator and stirrer. 40 grams of non-discrete multiwall carbon nanotubes, grade Flowtube 9000 from CNano corporation, are loaded into the reactor vessel while stirring the acid mixture and the temperature maintained at 85° C. The sonicator power is set at 130-150 watts and the reaction is continued for three hours. After 3 hours the viscous solution is transferred to a filter with a 5 micrometer filter mesh and much of the acid mixture removed by filtering using a 100 psi pressure. The filter cake is washed one time with four liters of deionized water followed by one wash of four liters of an ammonium hydroxide solution at pH greater than 9 and then two more washes with four liters of deionized water. The resultant pH of the final wash is 4.5. A small sample of the filter cake is dried in vacuum at 100° C. for four hours and a thermogravimetric analysis taken as described previously. The amount of oxidized species on the fiber is 2.4 percent weight and the average aspect ratio as determined by scanning electron microscopy to be 60. The residual catalyst content is determined as 2,500 ppm.

Example 3—Covalently Attaching a Dispersing Agent to Oxidized Single Wall Carbon Nanotube Using oxidized single wall carbon nanotubes from example 1 in the form of a wet cake with water of solids content 6.6% weight. 30.3 g of wet cake is mixed with 30 g of isopropanol then 3 g of Jeffamine M2005 monoamine terminated polyether dissolved in 350 g of isopropanol and 622 g water is added with stirring. Stirring is continued for 10 minutes. The slurry is transferred to a Waring Blender and blended at high speed for 10 minutes.

The slurry is then passed through a laboratory scale homogenizer keeping the temperature below 45° C. until no large structures >20 micrometers in scale are observed by optical microscopy.

The resultant mixture is then filtered using a Buchner filter and number 2 Whatman filter paper at 13 and washed 4 times with 100 cm$^3$ of 35% wt aqueous isopropyl alcohol. The washed wet cake is then dried first in a convection oven at 120° C. to 95% solids, then in a vacuum oven at 150° C. for 1 hour. This is termed SWNT MB in Table 1.

The TGA analysis run in nitrogen at 5° C./min in the range 200-600° C. gave 47% covalently bound polyether.

Example 4—Covalently Attaching a Dispersing Agent to Oxidized Multiwall Carbon Nanotube Using oxidized multiwall carbon nanotubes from example 2 in the form of a wet cake with water of solids content 5% weight. 40 g of wet cake is mixed with 30 g of isopropanol then 2 g of Jeffamine M2005 monoamine terminated polyether dissolved in 350 g of isopropanol and 622 g water is added with stirring. Stirring is continued for 10 minutes. The slurry is transferred to a Waring Blender and blended at high speed for 10 minutes.

The slurry is then passed through a laboratory scale homogenizer keeping the temperature below 45° C. until no large structures >20 micrometers in scale are observed by optical microscopy.

The resultant mixture is then filtered using a Buchner filter and number 2 Whatman filter paper at 13 and washed 4 times with 100 cm$^3$ of 35% wt. aqueous isopropyl alcohol. The washed wet cake is then dried first in a convection oven at 120° C. to 95% solids, then in a vacuum oven at 150° C. for 1 hour.

The TGA analysis run in nitrogen at 5° C./min in the range 200-600° C. gave 18% covalently bound polyether.

Example 5—Coating a Nylon Powder

Nylon 11 is ground into small powder granules less than 10 micrometers in diameter. A dispersion is made by taking 1 g of the carbon nanotubes of Example 4 in 200 g aqueous isopropanol alcohol (50/50) together with 1 g of polyvinylpyrrolidone, Molecular weight about 24,000 daltons (Sigma Aldrich). 100 g of the Nylon 11 powder is stirred into the modified carbon nanotube dispersion and stirred for 1 hour. The material is then dried in a convection oven at 110° C. The dried material is placed in a ball mill for 1 hour to give a fine dispersion of Nylon 11 with a coating of the dried dispersion.

The powder can then be used in an SLS additive manufacturing process to create strong parts with enhanced electrical conductivity with resistance less than 10 billion ohm per square. The coating of oxidized discrete carbon nanotubes with covalently attached dispersing agent allows for improved post sinter annealing of parts by infra-red or radio frequency radiation.

Example 6—Coating a Ceramic Powder

Using aluminum oxide powder granules less than 10 micrometers in diameter. A dispersion is made by taking 1 g of the carbon nanotubes of Example 4 in 200 g isopropanol alcohol together with 1 g Molecular weight about 24,000 daltons (Sigma Aldrich) and mixing in a Thinky mixer at 2000 rpm for 5 minutes. The dispersion is jetted selectively onto the layer of aluminum oxide powder and the alcohol is removed by drying.

The powder is bound by the dried dispersion of oxidized discrete carbon nanotubes and can then be sintered to create strong parts. The dispersion of oxidized discrete carbon nanotubes with covalently attached dispersing agent significantly improves the green strength of the ceramic part and the during sintering the covalently bound dispersing agent is removed. The oxidized discrete carbon nanotubes can be used to induce heating by electric/magnetic fields, or infrared or radio frequency radiation.

Example 7—Mixing of Radiation Curable Resin

Radiation curable compositions for vat photopolymerization are prepared by weighing ingredient and loading into a container. The mixture is mechanically stirred at room temperature or elevated temperatures (up to 80° C.) until a homogeneous resin mixture is obtained. The prepared compositions are processed in the vat photopolymerization equipment and fabricated specimens are analyzed in accordance with the test methods described below.

Fabrication of Three-Dimensional Specimens.

The general procedure used for preparing three-dimensional specimens with vat photopolymerization equipment is as follows. The radiation curable resin is poured into a vat. The fabrication parameters were set as standard-black resin and 25 μm layer thickness. In that mode, the resin is heated to 31° C. prior to part fabrication. Depending on the composition of the resin, a sufficient number of laser passes were employed to provide the desired polymerization energy. The material was exposed to a laser emitting in the range of 405 nm. Initially a "green part" is formed, in which layers are not completely cured. Under curing allows for the successive layers to better adhere by bonding when further cured. The fabricated "green part" is removed from the machine, washed with isopropyl alcohol, dried in air and post-cured in a curing chamber equipped with 405 nm multi-directional LED lamps. All specimens were post-cured in the curing chamber at room temperature for 30 minutes unless specified otherwise.

Test Methods

The resin is prepared to satisfy desired viscosity and wetting behavior requirements. Viscosity and wetting behavior directly affect the recoating depth (layer thickness before radiation exposure), which in turn influences the build resolution in z-direction. Viscosity data was collected on freshly prepared resins using HR20 Discovery Hybrid Rheometer (TA Instruments). The 40 mm 2.002° Stainless Steel Peltier plate was used for the flow sweep experiment. The logarithmic sweep was performed by sweeping the shear rate from $1.0e^{-3}$ to 8000 1/s at room temperature. Additional flow temperature ramp testing was conducted at a shear rate of 6 1/s and temperature ramp from 25° C. to 80° C. at ramp rate of 2° C./min. Table 2 shows the viscosity at zero shear rate for three example compositions. Data shows that viscosity increases exponentially with increase in oxidized discrete carbon nanotube with bonded dispersion agent content in the final resin formulation. Temperature ramp results are shown in Table 3 and provide comparison points at 25° C., 50° C., and 80° C. The results show that with increase in temperature the viscosity reduces exponentially at the constant shear rate.

TABLE 4

| Example | Viscosity at 25° C., [cP] |
|---|---|
| 7.1 | 2,093 |
| 7.2 | 14,084 |
| CONTROL 1 | 2,284 |

TABLE 5

| Example | Viscosity at 25° C., [cP] | Viscosity at 50° C., [cP] | Viscosity at 80° C., [cP] |
|---|---|---|---|
| 7.1 | 770 | 161 | 63 |
| 7.2 | 778 | 219 | 105 |
| CONTROL 1 | 2073 | 267 | 50 |

Table 6 lists the components of each photocurable composition labeled as Examples 7.1, 7.2 and Control 7.1. NOTE: TPO and OB amounts do not count towards total composition percentage.

TABLE 7

| Component | Example 7.1, [% by weight] | Example 7.2, [% by weight] | Control 1, [% by weight] |
|---|---|---|---|
| BR-952 | 47.00 | 37.00 | 67.00 |
| BR-371 | 7.00 | 7.00 | 7.00 |
| HEMA | 26.00 | 26.00 | 26.00 |
| TPO | 1.00 | 1.00 | 1.00 |
| OB | 0.00 | 0.00 | 0.06 |
| SWCNT MB | 20.00 | 30.00 | 0 |

Tensile data was collected by testing tensile Type IV specimens (ASTM D638) fabricated using vat photopolymerization equipment. All specimens were fabricated vertically. Tensile strength, Young's modulus, and elongation at break tests were conducted 24 hours or more after post-curing. The tensile tests were conducted in accordance with ASTM D638, which is hereby incorporated in its entirety by reference, except that no provision was made for controlling the room temperature and humidity and the bars were not equilibrated for 2 days. The testing was performed on an Instron testing machine (model 5985). The reported data is an average of three measurements. Table 8 shows the Ultimate tensile strength, yield strength, and young's modulus for example 7.1 and 7.2 compared to control that does not have oxidized discrete carbon nanotubes with bonded dispersing agent added to the composition. These examples show that addition of oxidized discrete carbon nanotubes with bonded dispersing agent increases both tensile and yield strength as well as Young's modulus compared to resin without the oxidized discrete carbon nanotubes.

TABLE 9

| Example | Tensile Strength, [MPa] | Yield Strength, [MPa] | Young's Modulus, [GPa] |
|---|---|---|---|
| 7.1 | 69 ± 0.1 | 53.0 ± 1.5 | 2.9 ± 0.05 |
| 7.2 | 67 ± 0.4 | 48.6 ± 0.6 | 2.8 ± 0.04 |
| CONTROL 1 | 63.7 ± 1 | 34.7 ± 0.8 | 2.1 ± 0.03 |

Cured specimens for determining the Izod impact strength were prepared in the same manner as for the tensile bars, except the specimens were designed in accordance with ASTM D-256A standard and had dimensions of 3.2 mm×12.7 mm×63.5 mm (thickness× width× length). Specimens were notched using a motorized notching cutter from Ray-Ran. Izod Impact was measured using Universal Pendulum Impact System by Ray-Ran equipped with 2.75 J pendulum. The reported data is the average of three measurements.

Impact strength of examples 7.1 to 7.4 is shown in Table 10. These examples show that addition of discrete oxidized carbon nanotubes with bonded dispersing agent significantly enhance the impact strength of the fabricated specimens compared to resin without the oxidized discrete carbon nanotubes.

TABLE 11

| Example | Impact Average, [J/m] | % Increase |
|---|---|---|
| 7.1 | 19.8 | 32 |
| 7.2 | 15.7 | 4 |
| 7.3 | 19.8 | 75 |
| 7.4 | 28.5 | 151 |
| CONTROL 1 | 15.0 | ** |
| CONTROL 2 | 11.3 | ** |

Table 12 lists the components of each photocurable composition labeled as Examples 7.3, 7.4 and Control 2.

TABLE 13

| Component | Example 7.3, [% by weight] | Example 7.4, [% by weight] | Control 2, [% by weight] |
|---|---|---|---|
| Formlabs Clear | 99.95 | 99.80 | 100.00 |
| MWCNT | 0.05 | 0.20 | 0.00 |

The invention claimed is:

1. An additive manufacturing dispersion wherein the dispersion comprises at least one portion of a cross-linkable moiety, and oxidized, discrete carbon nanotubes with a bonded dispersing agent on at least one sidewall of the oxidized discrete carbon nanotubes wherein the oxidized, discrete carbon nanotubes are present in the range of greater than zero and up to about 30% by weight based on the total weight of the dispersion and a plurality of the carbon nanotubes present in the dispersion are discrete.

2. The dispersion of claim 1 wherein the oxidized, discrete carbon nanotubes comprise an interior and exterior surface, each surface comprising an interior surface oxidized species content and an exterior surface oxidized species content, wherein the interior surface oxidized species content is at least about 0.01 up to 3 weight percent relative to carbon nanotube weight and wherein the interior surface oxidized species content differs from the exterior surface oxidized species content by at least about 20%, and as high as 100%.

3. The dispersion of claim 1 wherein the oxidized discrete carbon nanotubes comprise a mixture of oxidized discrete carbon nanotubes with a bimodal or trimodal distribution of the diameters of the oxidized discrete carbon nanotubes formed from combinations of oxidized discrete single wall, oxidized discrete double wall and oxidized discrete multi-wall carbon nanotubes.

4. The dispersion of claim 1 wherein the bonded dispersing agent on the sidewall of the oxidized discrete carbon nanotubes is covalently bonded.

5. The dispersion of claim 1 wherein the bonded dispersing agent on the sidewall of the oxidized discrete carbon nanotubes comprises an average molecular weight in the range of about 50 to about 20,000 daltons and the weight fraction of bonded dispersing agent on the sidewall of the discrete carbon nanotubes relative to the oxidized discrete carbon nanotubes is greater than about 0.02 and less than about 0.8.

6. The dispersion of claim 1 wherein the bonded dispersing agent on the sidewall of the oxidized discrete carbon nanotubes is miscible with a material in contact with the bonded dispersing agent.

7. The dispersion of claim 1 further comprising fillers in the percent by weight from about 0.1% to about 30% by weight of the dispersion selected from the group consisting of carbon black, graphene, oxidized graphene, reduced graphene, carbon fibers, silicas, silicates, halloysite, clays, calcium carbonate, wollastonite, glass, fire-retardants and talc.

8. The dispersion of claim 1 further comprising a member of the group consisting of thermoplastics, thermosets, and elastomers.

9. The dispersion of claim 1 further comprising a core shell elastomer further comprising particles diameters from about 0.01 to about 1 micrometer.

10. The dispersion of claim 1 further comprising semiconductor, metallic and, or ceramic powders with particle diameters from about 1 nm to about 20 micrometers.

11. The dispersion of claim 1 further comprising at least one additional dispersing agent attached to the sidewall of the oxidized discrete carbon nanotubes selected from the group consisting of anionic, cationic, nonionic and zwitterionic surfactants, polyvinyl alcohols, copolymers of polyvinyl alcohols and polyvinyl acetates, polyvinylpyrrolidones and their copolymers, carboxymethyl cellulose, carboxypropyl cellulose, carboxymethyl propyl cellulose, hydroxyethyl cellulose, polyetherimines, polyethers, starch, and mixtures thereof.

12. The dispersion of claim 1 wherein the oxidized discrete carbon nanotubes comprise about 0.1% to about 20% by weight of nitrogen atoms.

13. The dispersion of claim 1 wherein a part made by Additive Manufacturing has an electrical resistance less than 10 billion ohms per square.

14. The dispersion of claim 1 wherein the dispersion has a UV-visible absorption at 500 nm greater than about 0.5 units of absorbance for a concentration of oxidized discrete carbon nanotubes in the dispersion of $2.5 \times 10^{-5}$ g/ml.

15. The dispersion of claim 1 which further comprises a filler selected from the group of thermally conducting materials selected from the group consisting of metals and metal alloys, boron nitride, aluminum oxide, silicon nitride, aluminum nitride, diamond, graphite and graphene.

16. The dispersion of claim 1 further comprising a biologically reactive species selected from the group consisting of species that can interact with bacteria, virus, fungi, and biological agents.

17. An additive manufacturing dispersion for at least partially encapsulating electronic components, wherein the dispersion comprises:
at least one portion of a cross-linkable moiety; and
oxidized, discrete carbon nanotubes:
wherein the oxidized, discrete carbon nanotubes comprise a dispersing agent bonded on a sidewall of the oxidized, discrete carbon nanotubes; and
wherein the oxidized, discrete carbon nanotubes are present in the range of greater than zero and up to about 30% by weight based on the total weight of the dispersion; and
wherein a plurality of the carbon nanotubes present in the dispersion are discrete.

* * * * *